US010208311B2

(12) United States Patent
Syed

(10) Patent No.: US 10,208,311 B2
(45) Date of Patent: *Feb. 19, 2019

(54) METHOD FOR CONTROLLING OBESITY USING MINIMALLY INVASIVE MEANS

(71) Applicant: Mubin I. Syed, Springfield, OH (US)

(72) Inventor: Mubin I. Syed, Springfield, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/644,137

(22) Filed: Jul. 7, 2017

(65) Prior Publication Data

US 2017/0306328 A1    Oct. 26, 2017

Related U.S. Application Data

(62) Division of application No. 15/255,002, filed on Sep. 1, 2016, now Pat. No. 9,976,144, which is a division of application No. 15/000,769, filed on Jan. 19, 2016, now Pat. No. 10,053,693.

(51) Int. Cl.
| | |
|---|---|
| *A61K 48/00* | (2006.01) |
| *A61K 9/14* | (2006.01) |
| *C12N 7/00* | (2006.01) |
| *C12N 15/113* | (2010.01) |
| *A61K 33/42* | (2006.01) |
| *A61K 38/45* | (2006.01) |
| *A61M 25/01* | (2006.01) |
| *A61B 34/20* | (2016.01) |

(52) U.S. Cl.
CPC .......... *C12N 15/1137* (2013.01); *A61B 34/20* (2016.02); *A61K 9/14* (2013.01); *A61K 33/42* (2013.01); *A61K 38/45* (2013.01); *A61M 25/01* (2013.01); *C12N 7/00* (2013.01); *C12N 15/113* (2013.01); *C12Y 203/01* (2013.01); *A61B 2034/2051* (2016.02); *A61B 2034/2063* (2016.02); *C12N 15/1136* (2013.01); *C12N 2310/11* (2013.01); *C12N 2310/111* (2013.01); *C12N 2310/122* (2013.01); *C12N 2310/14* (2013.01); *C12N 2310/531* (2013.01); *C12N 2320/32* (2013.01)

(58) Field of Classification Search
CPC ........ A61K 9/14; C12N 7/00; C12N 2320/32; A61M 25/01
See application file for complete search history.

(56) References Cited

U.S. PATENT DOCUMENTS

| | | | |
|---|---|---|---|
| 8,617,132 | B2 | 12/2013 | Golzarian et al. |
| 9,089,541 | B2 | 7/2015 | Azamian et al. |
| 9,114,123 | B2 | 8/2015 | Azamian et al. |
| 9,114,124 | B2 | 8/2015 | Azamian et al. |
| 9,976,144 | B2 | 5/2018 | Syed |
| 10,053,693 | B2 | 8/2018 | Syed |
| 2005/0142202 | A1 | 6/2005 | Roorda et al. |
| 2007/0053830 | A1 | 3/2007 | Peng et al. |
| 2009/0053281 | A1 | 2/2009 | Richard |
| 2009/0053318 | A1 | 2/2009 | Tan et al. |
| 2010/0196396 | A1 | 8/2010 | Szentirmai et al. |
| 2011/0295179 | A1 | 12/2011 | Harris et al. |
| 2011/0295337 | A1 | 12/2011 | Albrecht et al. |
| 2012/0035249 | A1 | 2/2012 | Kuhn et al. |
| 2012/0213831 | A1 | 8/2012 | Vogel et al. |
| 2012/0215094 | A1 | 8/2012 | Rahimian et al. |
| 2013/0157936 | A1 | 6/2013 | Van Der Lely et al. |
| 2013/0184635 | A1 | 7/2013 | Levy et al. |
| 2014/0094734 | A1 | 4/2014 | Stack et al. |
| 2014/0179770 | A1 | 6/2014 | Zhang et al. |
| 2014/0194805 | A1 | 7/2014 | Levine et al. |
| 2014/0303543 | A1 | 10/2014 | Meade et al. |
| 2014/0364792 | A1 | 12/2014 | Stack et al. |
| 2015/0020223 | A1 | 1/2015 | Zhang et al. |
| 2015/0032085 | A1 | 1/2015 | Azamian et al. |
| 2015/0112332 | A1 | 4/2015 | Azamian et al. |
| 2015/0157565 | A1 | 6/2015 | Heartlein et al. |
| 2015/0223956 | A1 | 8/2015 | Nadler et al. |
| 2015/0232881 | A1 | 8/2015 | Glucksmann et al. |
| 2015/0272762 | A1 | 10/2015 | Cox et al. |
| 2015/0274634 | A1 | 10/2015 | Mazitscheck et al. |
| 2015/0297691 | A1 | 10/2015 | Goosens et al. |
| 2015/0359540 | A1 | 12/2015 | Kipshidze et al. |

(Continued)

FOREIGN PATENT DOCUMENTS

| | | |
|---|---|---|
| WO | WO 2012101524 | 8/2012 |
| WO | WO 2013/119800 | 8/2013 |
| WO | WO 2015/002931 | 1/2015 |

OTHER PUBLICATIONS

Pajak et al. Chennik 64,7-8, pp. 527-530 (Year: 2010).*
Kipshidze et al., First-in-Study of Left Gastric Artery Embolization for Weight Loss, Journal of American College of Cardiology, 2013, vol. 61(10), p. E2056.
Wellman et al., Knockdown of Central Ghrelin O-Acyltransferase by Vivo-Morpholino Reduces Body Mass of Rats Fed a High-Fat Diet, Peptides, 2015, vol. 70, pp. 17-22.
Yang et al., Inhibition of Ghrelin O-Acyltransferase (GOAT) by Octanoylated Pentapeptides, PNAS, 2008, vol. 105, pp. 10750-10755.

(Continued)

*Primary Examiner* — Brian Whiteman
(74) *Attorney, Agent, or Firm* — Jennifer Hayes; Nixon Peabody LLP

(57) ABSTRACT

Methods for controlling obesity using minimally-invasive procedures including introducing embolic crystal particles that are naturally occurring and mostly non-toxic salts into the arterial capillaries feeding the sections of the stomach where the appetite inducing hormone, ghrelin, is produced to limit the blood flow to the region reducing appetite; introducing a virus vector or antisense oligonucleotide to inhibit the production of ghrelin and reduce the appetite; and introducing a soluble embolic particle with a virus vector or antisense oligonucleotide which will inhibit the flow of blood initially and then dissolve and release the inhibit vector to the region, generating ghrelin to control the appetite.

19 Claims, 2 Drawing Sheets

(56) References Cited

U.S. PATENT DOCUMENTS

2017/0204409 A1 7/2017 Syed
2018/0127756 A1 5/2018 Syed

OTHER PUBLICATIONS

Andrade et al., Immunization Against Active Ghrelin using Virus-like Particles for Obesity Treatment, Current Pharmaceutical Design, 2013, vol. 19(36), pp. 6551-6558.
Arepally et al., Catheter-Directed Gastric Artery Chemical Embolization Suppresses Systemic Ghrelin Levels in Porcine Model, Radiology, 2008, vol. 249, pp. 127-133.
Bawudun et al., Ghrelin Suppression and Fat Loss after Left Gastric Artery Embolization in Canine Model, Cardiovascular Intervent Radiology, 2012, vol. 35, pp. 1460-1466.
Gunn et al., A Preliminary Observation of Weight Loss Following Left Gastric Artery Embolization in Humans, Hindawi Publishing Corporation, Journal of Obesity, 2014, vol. 2014, 4 pages.
Kubo et al., Hydroxyapatite Ceramics as a Particulate Embolic Material: Report of the Physical Properties of Hydroxyapatitie Particles and the Animal Study, AJNR Am J Neuroradiol, 2003, vol. 24, pp. 1540-1544.
Paxton et al., Bariatric Embolization for Suppression of the Hunger Hormone Ghrelin in a Porcine Model, Radiology, 2013, vol. 266(2), pp. 471-479.
Pelage, Opinion: A Review of Current Embolic Agents, Interventional News, 2009, 2 pages.
Rao et al., siRNA vs shRNA: Similarities and Differences, Advanced Drug Delivery Reviews, 2009, vol. 61, pp. 746-775.
Wagh, Review Article: Recent Progress in Chemically Bonded Phosphate Ceramics, ISRN Ceramics, 2013, vol. 2013, 20 pages.
Weiss et al., Effect of Bariatric Embolization on Various Appetite-Driving Hormones of Obesity Annual Scientific Meeting European Society, 2014.
Weiss, Clifford R., et al., Bariatric Embolization of the Gastric Arteries for the Treatment of Obesity, Journal of Vascular Intervention, 2015.
International Search Report and Written Opinion for PCT/US2016/024797 dated Jul. 12, 2016, 12 pages.
Angrisani et al., Bariatric Surgery Worldwide 2013, Obesity Surgery, 2015, vol. 25(10), pp. 1822-1832.
Bookstein et al., Transcatheter Hemostasis of Gastrointestinal Bleeding using Modified Autogenous Clot, Radiology, 1974, vol. 113(2), pp. 277-285.
Cummings et al., Gastrointestinal Regulation of Food Intake, Journal of Clinical Invest., 2007, vol. 117, pp. 13-23.
Diana et al., Embolization of Arterial Gastric Supply in Obesity (EMBARGO): an Endovascular Approach in the Management of Morbid Obesity. Proof of the Concept in the Porcine Model, Obesity Surgery, 2015, vol. 25(3), pp. 550-558.
Diana et al., Gastric Supply Manipulation to Modulate Ghrelin Production and Enhance Vascularization to the Cardia; Proof of the Concept in a Porcine Model, Surgical Innovation, 2015, vol. 22, pp. 5-14.
Gagner et al., Fifth International Consensus Conference: Current Status of Sleeve Gastrectomy, Surgery for Obesity and Related Diseases, 2016, vol. 12(4), pp. 750-756.
Kipshidze et al., Endovascular Bariatrics: First in Humans Study of Gastric Artery Embolization for Weight Loss, JACC Cardiovascular Interventions, 2015, vol. 8, pp. 1641-1644.
Masters et al., The Impact of Obesity on US Mortality Levels: The Importance of Age and Cohert Factors in Population Estimates, American Journal of Public Health, 2013, vol. 103(10), pp. 1895-1901.
Morris et al., Embolization of the Left Gastric Artery in the Absence of Angiographic Extravasation, Cardiovascular and Interventional Radiology, 1986, vol. 9, pp. 195-198.
Murphy et al., Gut Hormones in the Control of Appetite, Experimental Physiology, 2004, vol. 89, pp. 507-516.
Ng et al., Global, Regional and National Prevelance of Overweight and Obesity in Children and Adults 1980-2013: A Systematic Analysis, Lancet, 2014, vol. 384(9945), pp. 766-781.
Paxton et al., Histopathologic and Immunohistochemical Sequelae of Bariatic Embolization in a Porcine Model, Journal of Vascular Interval Radiology, 2014, vol. 25(3), pp. 455-461.
Perry et al., Appetite Regulation and Weight Control, the Role of the Gut Hormones, Nutrition and Diabetes, 2012, vol. 2(e26), pp. 1-7.
Remedios et al., Bariatric Nutrition Guidelines for the Indian Population, Obesity Surgery, 2016, vol. 26(5), pp. 1057-1068.
Rosch et al., Selective Arterial Ambolization. A New Method for Control of Acute Gastrointestinal Bleeding, Radiology, 1972, vol. 102, pp. 303-306.
Shiiya et al., Plasma Ghrelin Levels in Lean and Obese Humans and the Effect of Glucose on Ghrelin Secretion, Journal of Clinical Endocrinology and Metabolism, 2002, vol. 87, pp. 240-244.
Stegenga et al., Identification, Assessment and Management of Overweight and Obesity: Summary of Updated NICE Guidance, BMJ, 2014, vol. 349, pp. 32-37.
Syed et al., Gastric Artery Embolization Trial for the Lessening of Appetite Nonsurgically (GET LEAN): Six-Month Preliminary Data, Journal of Vascular Intervention Radiology, 2016, vol. 27, pp. 1502-1508.
Syed et al., Bariatric: Embolization for Obesity: A New Frontier for Interventional Medicine, Endovascular Today, 2017, vol. 16(4), pp. 78-82.
Weiss et al., Clinical Safety of Bariatric Arterial Embolization: Preliminary Results of the BEAT Obesity Trial, Radiology, 2017, vol. 283(2), pp. 598-608.
Youdim A., The Clinician's Guide to the Treatment of Obesity, New York: Springer, 2015.
Yousseif et al., Differential Effects of Laparoscopic Sleeve Gastrectomyand Laparoscopic Gastric Bypass on Appetite, Circulating Acyl-ghrelin, Peptide YY3-36 and Active GLP-1 Levels in Non-diabetic Humans, Obesity Surgery, 2014, vol. 24, pp. 241-252.

* cited by examiner

```
┌─────────────────────────────────────────────────────────────────────┐
│    Prepare and powder Potassium Di-hydrogen Phospate (KH2PO4) salt  │
└─────────────────────────────────────────────────────────────────────┘
                                  │                              S2001
                                  ▼
┌─────────────────────────────────────────────────────────────────────┐
│    Make a saturated solution of KH2PO4 in water at 80 to 90 degree Fahrenheit │
└─────────────────────────────────────────────────────────────────────┘
                                  │                              S2002
                                  ▼
┌─────────────────────────────────────────────────────────────────────┐
│  Add Magnessium Hydroxide (MgOH) to the solution to increase the PH value in │
│                      the range of 5.5 and 6                         │
└─────────────────────────────────────────────────────────────────────┘
                                  │                              S2003
                                  ▼
┌─────────────────────────────────────────────────────────────────────┐
│           Add any inhibit / viral vectors to be encapsulated         │
└─────────────────────────────────────────────────────────────────────┘
                                  │                              S2004
                                  ▼
┌─────────────────────────────────────────────────────────────────────┐
│  Cool the solution at a rate to form crystals of a required size range (300 to 600 │
│                               microns)                              │
└─────────────────────────────────────────────────────────────────────┘
                                  │                              S2005
                                  ▼
┌─────────────────────────────────────────────────────────────────────┐
│            The crystals are ground or tumbled to remove sharp edges │
└─────────────────────────────────────────────────────────────────────┘
                                  │                              S2006
                                  ▼
┌─────────────────────────────────────────────────────────────────────┐
│  Crystals are sieved to ensure the applicable range of sizes for the resultant │
│                            embolic particles                        │
└─────────────────────────────────────────────────────────────────────┘
                                  │                              S2007
                                  ▼
┌─────────────────────────────────────────────────────────────────────┐
│  The dried embolic particles are used to form a colloidal solution with dilute │
│         iodine contrast solution for treatment of obesity by embolization │
└─────────────────────────────────────────────────────────────────────┘
                                                                 S2008
```

Fig. 2

METHOD FOR CONTROLLING OBESITY USING MINIMALLY INVASIVE MEANS

CROSS-REFERENCE TO RELATED APPLICATIONS

This application is a divisional application of U.S. patent application Ser. No. 15/255,002, filed Sep. 1, 2016, which is a divisional application of U.S. patent application Ser. No. 15/000,769, filed Jan. 19, 2016, the entire disclosure of which is incorporated herein by reference in its entirety.

BACKGROUND

1. Field

The invention relates to methods for controlling and treating obesity using non-surgical means and specifically by reduction of or inhibition of the production of ghrelin the apitize generating hormone.

2. Related Art

Obesity has become an epidemic problem in Western societies contributing to several disease processes including metabolic diseases, hypertension, and cardiovascular disease. Adipogenesis is defined as the formation of fat or fatty tissue, the development of fat cells from pre-adipocytes. Obesity is a severe chronic syndrome characterized by excessive accumulation of fat. Patients with abdominal obesity are often prone to diseased conditions such X-syndrome (insulin resistant diabetes, Type 2 diabetes, hypertension, and disorders of lipid metabolism), and abdominal obesity becomes one of the potent risk factors of early arteriosclerosis, ischemic heart disease, and cerebrovascular disease.

Urbanization of countries' populations with associated sedentary lifestyles and intake of rich foods on a normal basis has led to an increase in obesity in the general population. The chronic obese segment of the population now stands close to 30% in the US and other developed countries. This has created an increase in associated illnesses leading to increase in health care costs across these countries.

There are multiple aims for treatment for obesity. A first aim is to reduce weight by burning excessive fat or reduce absorption of food that can be converted to fat; a second aim is to improve a metabolic imbalance in patients.

Today, there are a number of surgical methods for treatment of obesity, such as an implantable balloon device to stretch the stomach wall and simulate satiety during eating, thereby reducing the amount of food intake of the patient. Another surgical method used to reduce food intake and absorption requires reducing the size of the stomach itself by using gastric band with or without electrical stimulation, removal of part of the intestines to reduce food absorption, etc. Though these surgical methods have been available for control of obesity for some time now, the number of even acutely obese patients who opt for such procedures have been very small and hence the success of controlling obesity in the general population by these methods have been limited.

Alternate treatment by medication has also been proposed to limit and control food intake and absorption. Most of these medications have side effects that are not acceptable to the using public. Hence, this type of treatment has also not been too well received.

Since obesity has been recognized as a major problem, other methods for controlling it, that are more acceptable to the public have been under investigation and need to be identified. A large number of studies have focused on use of chemical agents and gene identification aspects to control obesity. Others have looked at nerve excitation and sensation removal as treatment for obesity.

Accordingly, what is needed is a non-surgical way, that is minimally invasive, to treat obesity that is acceptable to the obese population and can be easily implemented.

SUMMARY

The following summary of the invention is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

In accordance with one aspect of the invention, a method of treating obese patients is disclosed that includes delivering embolic particles to targeted ghrelin production sites.

The embolic particles may be virus vectors embedded in the embolic particles. The embolic particles may be antisense inhibitors embedded in the embolic particles. The embolic particles may reduce blood flow at the targeted ghrelin production sites. The embolic particles may reduce blood flow at the targeted ghrelin production sites and the virus vectors may sustain reduced production of ghrelin. The embolic particles may reduce blood flow at the targeted production sites and the antisense inhibitors sustain reduced production of ghrelin. The embolic particles may be magnesium phosphate. The embolic particles may be calcium di-hydrogen phosphate. The embolic particles may be potassium di-hydrogen phosphate.

The embolic particles may be delivered using a percutaneously introduced catheter guided to the targeted ghrelin production sites using an imaging technique. The imaging technique may be selected from the group consisting of x-ray fluorescence or ultrasound tracking.

The size of the embolic particles may be between 300 and 500 microns.

In accordance with another aspect of the invention, a method of treating obese patients is disclosed that includes delivering modified virus vectors to targeted ghrelin production sites.

The method may further include delivering embolic particles to the targeted ghrelin production sites.

The virus vectors may be delivered using a percutaneously introduced catheter guided to the targeted ghrelin production sites using an imaging technique.

The imaging technique may be selected from the group consisting of x-ray fluorescence or ultrasound tracking.

In accordance with a further aspect of the invention, a method of treating obese patients is disclosed that includes delivering modified antisense oligonucleotide to targeted ghrelin production sites.

The antisense oligonucleotide may include shRNA, and the method may further include using synthesized SiRNA to generate the shRNA.

The antisense oligonucleotide may be ghrelin-O-aclytransferase (GOAT). The method may further include delivering embolic particles to the targeted ghrelin production sites.

The virus vectors may be delivered using a percutaneously introduced catheter guided to the targeted ghrelin production sites using an imaging technique. The imaging technique may be selected from the group consisting of x-ray fluorescence or ultrasound tracking.

BRIEF DESCRIPTION OF THE DRAWINGS

The accompanying drawings, which are incorporated into and constitute a part of this specification, illustrate one or more examples of embodiments and, together with the description of example embodiments, serve to explain the principles and implementations of the embodiments.

FIG. 2 is a block diagram showing a method for controlling obesity in accordance with one embodiment of the invention.

DETAILED DESCRIPTION

Figure 1:
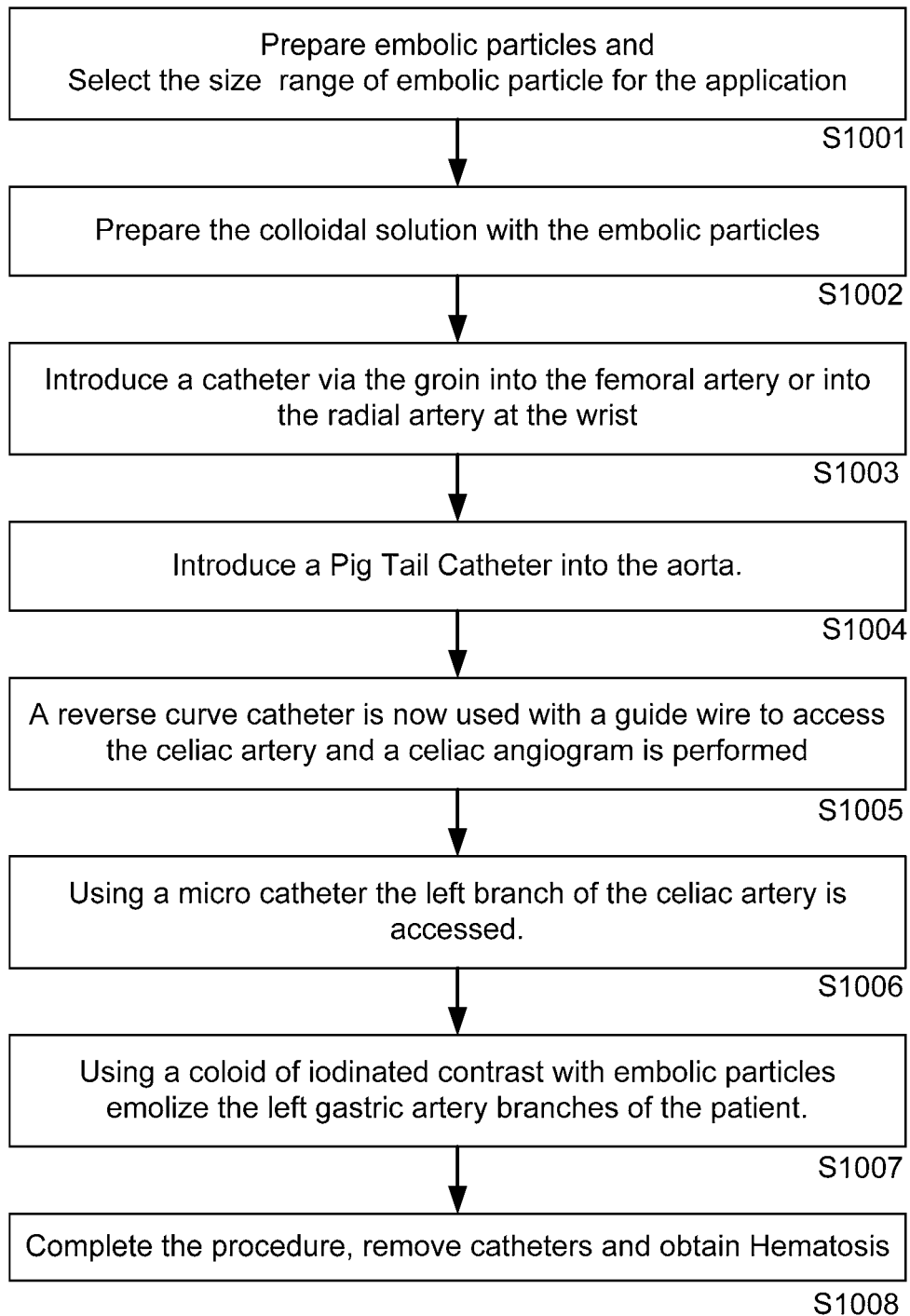
FIG. 1 is a block diagram showing a method for controlling obesity in accordance with one embodiment of the invention.

Obesity has been identified as a contributing factor to many of the diseases of the present day. Obesity is a medical condition in which excess body fat has accumulated to the extent that it may have an adverse effect on health, leading to reduced life expectancy and/or increased health problems. Obesity is a leading preventable cause of death worldwide, with increasing prevalence in adults and children, and authorities view it as one of the most serious public health problems of the 21st century. Obesity increases the risk of many physical and mental conditions. Excessive body weight is associated with various diseases, particularly cardiovascular diseases, diabetes mellitus type 2, obstructive sleep apnea, certain types of cancer, and osteoarthritis. As a result, obesity has been found to reduce life expectancy. These diseases are either directly caused by obesity or indirectly related through mechanisms sharing a common cause such as a poor diet or a sedentary lifestyle. Current solutions are mostly invasive in nature and hence have had a very difficult time finding acceptance from the obese community.

Leptin and ghrelin are considered to be complementary in their influence on appetite, with ghrelin produced by the stomach modulating short-term appetitive control (i.e., to eat when the stomach is empty and to stop when the stomach is stretched). Leptin is produced by adipose tissue to signal fat storage reserves in the body, and mediates long-term appetitive controls (i.e., to eat more when fat storages are low and less when fat storages are high). While these appetite mediating adipokines are produced peripherally, they control appetite through their actions on the central nervous system. In particular, they and other appetite-related hormones act on the hypothalamus, a region of the brain central to the regulation of food intake and energy expenditure and include the lateral hypothalamus and ventromedial hypothalamus, that are the brain's feeding and satiety centers. In some recent studies the effect of ghrelin has been found to have a significant impact on the eating habits and development of obesity in individuals.

Embodiments of the invention are directed to methods for reducing or inhibiting the production of ghrelin and other similar compounds in the human body, thereby reducing the short term urge for food intake to control obesity. Embodiments of the invention also reduce or inhibit leptin production. The disclosed methods are minimally invasive and hence are expected to be more acceptable as treatment by a wider group of obese patients.

Embodiments of the invention are directed to minimally invasive methods that might be more acceptable to the obese population for the treatment of obesity. In one embodiment, embolic particles of naturally occurring and non-toxic magnesium phosphate, calcium di-hydrogen phosphate and/or potassium di-hydrogen phosphate are introduced into the arterial capillaries feeding the sections of the stomach where the appetite inducing hormone, ghrelin, is produced to limit or inhibit the blood flow to the region. This reduces or destroys the cells that produce ghrelin and thereby reduce the short term appetite. Over a short period of time alternate capillaries will re-establish blood flow to the region but the destroyed cells will not re-generate within such period, enabling control of appetite and hence obesity of the individual. Typical introduction method for the embolic particles is by means of a catheter of the appropriate size, percutaneously introduced and guided using xray fluorescence or ultrasound tracking methods to the location. Once at the location the embolic particles are released into the blood stream in appropriate quantities required to block the blood flow to the regions generating ghrelin.

These magnesium phosphate, calcium di-hydrogen phosphate and potassium phosphate particles have multiple advantageous for bariatric embolization over other similar embolic particles. For example, in the case of potassium and calcium salts, the PH value of the solution may be adjusted using magnesium hydroxide or calcium hydroxide.

In particular, they are easily manufacturable in the required sizes for use as embolic particles, typically in the range between about 50 to 700 micro meters in size. In one particular embodiment, the embolic particle size is any value or range of values between about 300 to 500 micrometers.

Magnesium phosphate, calcium di-hydrogen phosphate and potassium di-hydrogen phosphate are also a naturally occurring compound in nature that is non-toxic in human applications. This reduces any adverse reactions to the use in treatments of the embolic particles.

Additionally, the structure of the magnesium phosphate, calcium di-hydrogen phosphate and potassium di-hydrogen phosphate particles are more regular and smooth than some of the other particles used in other applications as embolic particles. These particles, due to their shape, are able to reduce unnecessary trauma to the arterial walls of the vessels through which they are introduced.

Adding magnesium to the embolic particle as magnesium phosphate or adjusting the PH of the embolic particle forming solution by adding magnesium hydroxide provides additional advantages. Magnesium has the characteristics of enhancing the formation of capillaries. This allows for re-establishment of blood flow to the treated regions of the body faster for enabling recovery of the required functionality.

Magnesium phosphate is a compound that typically dissolves over time and can be used as a source inhibit vectors that are released over time into the blood stream feeding the target cells. Calcium di-hydrogen phosphate on the other hand is more stable and remains in system for a longer time, reducing the re-growth of the targeted cells.

In another embodiment, a virus vector or an antisense oligonucleotide is introduced to inhibit the production of ghrelin in conjunction with the embolization and reduce the appetite. The use of virus vectors, antisense oligonucleotide and Clustered Regularly Interspaced Short Palindromic Repeats (CRISPRs) have been used in the past for enhancing or inhibiting the production of various proteins or nucleic acid. It is possible to design a targeted delivery of the virus vectors or antisense oligoneucleotide to the target location within a gene to replace targeted segments of the gene associated with production of ghrelin. The silencing, or inactivation, of the targeted generation can be effected by cleaving the targeted nucleic acid sequence or replacement of the targeted RNA sequence by the alternate gRNA sequence. The delivery of the vector itself can be accomplished similar to the method of delivery of the embolic particles. A catheter of the appropriate size is percutaneously introduced and guided using x-ray fluorescence or ultrasound tracking methods to the treatment location. Once at the location, the virus vectors are released into the blood stream in appropriate quantities enabling substitution of the target RNA segment in the gene at the location to inhibit or stop production of ghrelin. Introducing a soluble embolic particle containing a virus vector or an antisense oligonucleotide which will inhibit the flow of blood initially and then dissolve, releasing the inhibit vector or antisense to the region generating ghrelin, provides a longer term control of ghrelin generation and control of the patient's appetite.

In some embodiments, short RNA strands may be used to achieve the result of suppressing the ghrelin production.

Small interfering RNA (siRNA) is an intermediate step in the RNA interference (RNAi) pathway. RNAi is a natural process the cells use to turn off unwanted genes. The siRNA is a double strand of 20 to 25 molecules that can bind to an RNA-induced silencing complex RNA. This siRNA cleaves the gene such that it stops producing the unwanted protein. The siRNA may be synthesized and used as a ghrelin inhibitor.

Similarly, a DNA construct may be delivered to the nucleus of a cell using a virus to enable the target cells to produce a short hairpin (shRNA) which can act as the inhibitor to the target protein. This shRNA may be also be used as a ghrelin inhibitor.

In another embodiment, the use of the embolic particle with the release at the target site of the inhibit vector are combined. The combination is advantageous because it provides a more appropriate and long term solution. In this embodiment, an embolic particle that dissolves over time is embedded within the inhibit vector or antisense oligonucleotide. The embolic particle is initially used to reduce the blood flow to the target location. This reduces the production of ghrelin as described above. Over time, the embolic particle dissolves away releasing the inhibit vector or antisense oligonucleotide into the target area in small doses to limit the regeneration and production of ghrelin over a long period of time. In one particular embodiment, the antisense oligonucleotide is ghrelin-O-acyltransferase (GOAT).

The use of potassium di-hydrogen phosphate as the base salt has the advantage that the dissolution rate of the crystal (embolic particular) during use is slow, enabling slow release of any inhibit vectors embedded therein while providing long term embolization of the region. The use of calcium di-hydrogen phosphate as the embolic particle dissolves away faster than the potassium di-hydrogen phosphate and it use is limited to short term embolization of the region followed by deliver of inhibit vectors to the correct location.

In each of the embodiments described above, the short term appetite is reduced with a direct impact on the obesity of the person treated. Although the techniques for treatment of obesity discussed herein are directed to the control of production of ghrelin, it will be appreciated that the treatment techniques disclosed herein may also be used for the long term appetite inducer leptin to further improve the treatment of obesity.

An exemplary procedure for use of embolic particles for obesity treatment (Bariatric embolization) is described briefly with reference to FIG. 1. It will be appreciated that the embolic particle may or may not contain inhibit vectors attached to the surface or embedded within to allow for slow release as the particle dissolves, as described above.

The process begins by preparing the embolic particles and choosing the right size range of the particles for use (block S1001).

The process continues by preparing the colloidal solution of embolic particles, with iodinated contrast material added for contrast, for bariatric embolization of the patient (block S1002).

The process continues by puncturing the groin at the common femoral artery (or puncture the radial artery in the wrist) for introduction of a catheter, with ultrasound and fluoroscopic guidance (block S1003).

The process continues by introducing a pigtail catheter into the aorta with aortagram (AP and lateral projection) for control (block S1004).

The celiac artery is selected using a reverse curve catheter with a guide wire and a celiac angiogram is performed to get correct data on the access to the left gastric artery branch of the celiac artery (block S1005).

The left gastric artery branch of the celiac artery is selected typically using a microcatheter (block S1006). This can be done with or without selection of this artery using the reverse curve catheter. It will be appreciated that a 0.014 inch guide wire may used in addition to or as a substitute for the microcatheter.

The process continues by using dilute iodinated contrast and using a colloidal form of embolic particles prepared to embolize the left gastric artery branches using the particles to limit or stop production of ghrelin and treat the patient for obesity (block S1007).

The process continues by removing the catheters and obtaining hemostasis using normal steps employed for the purpose (block S1008).

An exemplary preparation process for embolic particles with embedded embolization vectors and without embolization vectors is briefly described with reference to FIG. 2.

The typical chemical compound for creation of the embolic particle, with which the process is explained, is potassium di-hydrogen phosphate ($KH_2PO_4$) or calcium di-hydrogen phosphate ($CaH_2PO_4$). The solution of ($KH_2PO_4$) or ($CaH_2PO_4$) in water has a PH value near 4.2 which is not very suitable for bariatric embolization. Though $KH_2PO_4$/$CaH_2PO_4$ use is detailed, magnesium can be used instead as the base salt for making the embolic particle. Since magnesium provides advantages of capillary re-growth etc., adding magnesium hydroxide to get the PH value of the prepared solution to the range of 5.5 to 6, which is suitable for bariatric embolization, is typically preferred. As shown in FIG. 2, the process for preparation of the embolic particle is as follows:

The process begins by providing a powder potassium or calcium di-hydrogen phosphate (KH2PO4 or CaH2PO4) salts in solution (block S2001). This solution typically has a PH value in the range of 4.2 to 4.7, which is not suitable for use in bariatric embolization.

The process continues by making a saturated solution of the salt in water heated to 80 to 90 Fahrenheit while stirring continuously to make the salts dissolve fully (block S2002).

The process continues by mixing magnesium hydroxide (MgOH) solution preferably (or calcium hydroxide solution) to the above prepared solution to change its PH value to between 5.5 and 6.0 which is suitable for bariatric usage (block S2003). Mixing magnesium hydroxide to the solution has the effect of replacing some of the potassium or calcium in the solution with magnesium, in addition to changing the PH value.

As an optional step, any vectors that need to be incorporated into the embolic particles are added into the solution in quantities predetermined to be appropriate to get the concentration of the inhibit vectors in the embolic particles (block S2004).

The resultant solution is cooled at a rate sufficient enough to generate crystals typically in the range of 300 to 600 micron size from the solution (block S2005).

The crystals are tumbled/ground to remove the rough edges and achieve a more spherical form, in order to prevent trauma to the arterial walls during use (block S2006).

The crystals are sieved to optimize the size range, typically a rage within 300 to 500 microns, (the exact value or range can vary with the patient and the treatment parameters) required for the bariatric embolization application (block S2007).

A colloidal solution of the embolic particles with dilute iodine contrast solution is prepared and used for bariatric embolization (block S2008). For example, the process of FIG. 1 can be used for the bariatric embolization; it will be appreciated that other processes may be used for the bariatric embolization.

Even though the techniques for treatment of obesity discussed herein are directed to the control of production of ghrelin, similar treatments may also be provided for the long term appetite inducer leptin to further improve the treatment of obesity. It is understood that it is possible to use modifications of the methods disclosed to treat other problems in human patients that are treatable by inhibition or increase of specific protein production by cells in the body. Such modifications of the disclosed method, which will be well understood by practitioners of the art, though not explicitly covered, are also covered by this application.

As will be understood by those familiar with the art, the invention may be embodied in other specific forms without departing from the spirit or essential characteristics thereof. Likewise, the particular naming and division of the members, features, attributes, and other aspects are not mandatory or significant, and the mechanisms that implement the invention or its features may have different structural construct, names, and divisions. Accordingly, the disclosure of the invention is intended to be illustrative, but not limiting, of the scope of the invention.

While the invention has been described in terms of several embodiments, those of ordinary skill in the art will recognize that the invention is not limited to the embodiments described, but can be practiced with modification and alteration within the spirit and scope of the appended claims. The description is thus to be regarded as illustrative instead of limiting. There are numerous other variations to different aspects of the invention described above, which in the interest of conciseness have not been provided in detail. Accordingly, other embodiments are within the scope of the claims.

The invention has been described in relation to particular examples, which are intended in all respects to be illustrative rather than restrictive. Those skilled in the art will appreciate that many different combinations will be suitable for practicing the present invention. Other implementations of the invention will be apparent to those skilled in the art from consideration of the specification and practice of the invention disclosed herein. Various aspects and/or components of the described embodiments may be used singly or in any combination. It is intended that the specification and examples be considered as exemplary only, with a true scope and spirit of the invention being indicated by the following claims.

What is claimed is:

1. A method of treating an obese patient comprising:
   delivering modified virus vectors configured to target ghrelin producing cells to inhibit ghrelin production, wherein the modified virus vectors are embedded within dissolvable embolic particles that dissolve over time in human blood, to targeted ghrelin production sites,
   wherein a size of the dissolvable embolic particles, made from a solution of one or a mixture of salts selected from magnesium phosphate, calcium di-hydrogen phosphate, potassium di-hydrogen phosphate, that dissolve over time in blood, is between 300 and 500 microns.

2. The method of claim 1, wherein the embolic particles comprise magnesium phosphate, wherein the PH value is adjusted by magnesium hydroxide or calcium hydroxide added to a solution of magnesium phosphate from which the embolic particles are made.

3. The method of claim 1, wherein the embolic particles comprise calcium di-hydrogen phosphate, wherein the PH value is adjusted using magnesium hydroxide or calcium hydroxide added to a solution of calcium di-hydrogen phosphate from which the embolic particles are made.

4. The method of claim 1, wherein the embolic particles comprise potassium di-hydrogen phosphate, wherein the PH value of a solution of potassium di-hydrogen phosphate from which the embolic particles are made is adjusted using magnesium hydroxide or calcium hydroxide.

5. The method of claim 1, wherein the dissolvable embolic particles, that dissolve over time in the blood, containing the modified virus vectors are delivered using a percutaneously introduced catheter guided to the targeted ghrelin production sites using an imaging technique.

6. The method of claim 5, wherein the imaging technique is selected from the group consisting of x-ray fluorescence or ultrasound tracking.

7. The method of claim 1, wherein the dissolvable embolic particles release the modified virus vectors into the blood stream, as they dissolve over time in the blood.

8. A method of treating an obese patient, the method comprising:
   embedding modified virus vectors that inhibit ghrelin production in dissolvable embolic particles made from, one of, or a mixture of, magnesium phosphate, calcium di-hydrogen phosphate, or potassium di-hydrogen phosphate, wherein a PH value of the embolic particles is adjusted for minimally invasive non-toxic application in the obese human patient by addition of magnesium hydroxide or potassium hydrogen phosphate to the solution from which the embolic particles are made;
   delivering the embolic particles with the embedded modified virus vectors to the ghrelin production sites in the obese human patient using a percutaneously introduced catheter;
   wherein the modified virus vectors are delivered to targeted ghrelin production sites using the embolic particles that release the modified virus vectors as the embolic particles dissolve in blood over time.

9. The method of claim 8, wherein the embolic particles initially reduce blood flow at the targeted ghrelin production sites to destroy cells generating ghrelin and then dissolve away to re-establish normal blood flow to the site; wherein the destroyed ghrelin producing cells do not re-generate.

10. The method of claim 8, wherein the embolic particles initially reduce blood flow at the targeted ghrelin production sites to destroy cells generating ghrelin and over time dissolve away re-establishing normal blood flow to the site; wherein the dissolving embolic particles release the modified virus vectors embedded therein to limit ghrelin production from any remaining ghrelin producing cells.

11. The method of claim 8, wherein the embolic particles reduce blood flow at the targeted ghrelin production sites and wherein the virus vectors embedded in the embolic particles sustain a reduced production of ghrelin as the virus vectors are released over time and as the embolic particles dissolve.

12. The method of claim 8, wherein the embolic particles have a size between 300 and 500 microns and comprise magnesium phosphate.

13. The method of claim 8, wherein the embolic particles have a size between 300 and 500 microns and comprise calcium di-hydrogen phosphate.

14. The method of claim 8, wherein the embolic particles have a size between 300 and 500 microns and comprise potassium di-hydrogen phosphate.

15. The method of claim 10, wherein the embolic particles have a size between 300 and 500 microns and the embolic particles are PH adjusted for human use.

16. The method of claim 10, wherein the embolic particles reduce blood flow at the targeted ghrelin production sites, and wherein the virus vectors as they get released over time into the blood stream sustain reduced production of ghrelin.

17. The method of claim 8, wherein the virus vector is delivered using a percutaneously introduced catheter and guided through the arteries to the targeted ghrelin production sites using an imaging technique.

18. The method of claim, 17, wherein the imaging technique is selected from the group consisting of x-ray fluorescence or ultrasound tracking.

19. A method of treating an obese patient, the method comprising:
delivering modified virus vectors, that act to inhibit a production of ghrelin by the cells that produce ghrelin in a human body, contained within dissolvable embolic particles that dissolve over time in human blood, to targeted ghrelin production sites,
wherein the dissolvable embolic particles are made from, one of, or a mixture of, magnesium phosphate, calcium di-hydrogen phosphate, or potassium di-hydrogen phosphate, and
wherein a PH value of the dissolvable embolic particles is adjusted using magnesium hydroxide or calcium hydroxide.

* * * * *